United States Patent [19]

Dietz et al.

[11] 4,311,528

[45] Jan. 19, 1982

[54] ROOT FILLING PASTE FOR DENTAL SURGERY

[76] Inventors: Georg Dietz, Mauerkircher Str. 120, 8000 München 81; Hans-Helmut Barth, Jäcklinstr. 21, München 83, both of Fed. Rep. of Germany

[21] Appl. No.: 175,825

[22] Filed: Aug. 5, 1980

[30] Foreign Application Priority Data

Aug. 13, 1979 [DE] Fed. Rep. of Germany ....... 2932738

[51] Int. Cl.$^3$ ............................................... C09K 3/00
[52] U.S. Cl. ..................................... 106/35; 433/228
[58] Field of Search ........................... 106/35; 433/228

[56] References Cited

U.S. PATENT DOCUMENTS

| | | | |
|---|---|---|---|
| 2,516,438 | 7/1950 | Wheeler | 106/35 |
| 3,028,247 | 4/1962 | Molnar | 106/35 |
| 3,047,408 | 7/1962 | Dougherty | 106/35 |
| 3,367,788 | 2/1968 | Sheldon et al. | 106/35 |

*Primary Examiner*—Lorenzo B. Hayes
*Attorney, Agent, or Firm*—A. W. Breiner

[57] ABSTRACT

Disclosed is a root filling paste for dental surgery, containing calcium hydroxide, an X-ray contrast agent and oleum pedum tauri as the paste matrix or base, respectively. The addition of oleum pedum tauri permits the calcium hydroxide which could heretofore be filled into root canals with difficulty only, to be filled evenly and in sealingly filling manner into the root canals of gangrenous teeth. The anti-inflammatory and osteo-regenerating activity of calcium hydroxide may in this way come into effect regularly.

5 Claims, No Drawings

ROOT FILLING PASTE FOR DENTAL SURGERY

The present invention relates to a root filling paste for dental surgery, containing calcium hydroxide as the active component, an X-ray contrast agent and a pasty base.

The therapy of the chronic-periapical parodontitis and of the gangrene is nowadays still considered to be extremely complicated, and the rate of success of the treatment is relatively low. This low rate of success in the therapy of gangrene and chronic-periapical parodontitis is due primarily to the fact that complete elimination of the severe bacterial infection cannot be obtained, and alteration and healing of the acutely or chronically inflamed pariapical tissue does not result. It is mandatory for the successful treatment of gangrene and chronic-periapical parodontitis to provide, in addition to a complete filling of the dental root, an optimum medical treatment of the apex and of the periapical tissue in order to alter the acidic environments in the area of the chronically inflamed periapical tissue for the induction of the osteo-regenerating phase.

For the filling of gangrenous teeth affected by chronic periapical parodontitis, a great number of different medicaments are available. The most important ones of these medicaments which are most frequently used in the Western hemisphere, are the Walkhoff's paste, viz. a chlorophenol/camphor/menthol/iodoform paste (cf O. Walkhoff "Mein System der medikamentösen Behandlung schwerer Erkrankungen der Zahnpulpa und des Periodontiums", published by Verlag Meuser, Berlin 1928), the poly-antibiotic paste on the basis of varous antibiotics and of a liquid silicone as the pasty base or matrix (cf L. I. Grossmann "Lehrbuch der modernen Wurzelbehandlung", Medica Verlag Stuttgart 1968); the root filling paste N2 according to A. Sargenti (cf A. Sargenti "Rationelle Wurzelbehandlung", Quintessenz-Verlag 1968), and the root filling paste on the basis of calcium hydroxide developed by B. W. Hermann (cf B. W. Hermann in "Zahnärztl. Rdsch.", Vol. 39, page 888 (1930) and Medical Dissertation Würzburg 1920 "Calciumhydroxid als Mittel zum Behandeln and Füllen von Zahnwurzelkanälen").

The Walkhoff's paste is defective in that it is resorbed in the course of time after its application, such that dead spaces are formed. Accordingly, the Walkhoff's paste can be considered as a temporary resorbable filling material only. Apparent problems in the application of the poly-antibiotic paste include allergic reactions and generation of resistance in the case of chronically persisting germs. Problematic in the root filling paste N2 is its contents of paraformaldehyde of 4.7% which is close to the toxicity limit of 5% (see E. Sauerwein "Zahnerhaltungskunde", Thieme-Verlag Stuttgart 1972). Generally, calcium hydroxide may be used with good success for the filling of gangrenous teeth affected by chronic-periapical parodontitis, because calcium hydroxide, on the one hand, alkalizes the acidic inflamed areas and alters the acidic environments within the root canals to alkaline surroundings, with the result that inflammations are eliminated and a hard tissue barrier is gradually formed. A severe drawback of the conventional root filling pastes on the basis of calcium hydroxide, which contain, for example, Ringer's solution as the paste base or substrate, is their extremely inferior ability of being inserted into the root canals. This is due to the fact that such root filling pastes are highly brittle, apparently owing to the requisite high contents of calcium hydroxide. As indicated above, complete filling of the root canals is therefore substantially not possible in practice.

Still further, the determination of the degree of filling of the root canals gives rise to difficulty when using root filling pastes on the basis of calcium hydroxide, due to the lacking X-ray contrast of calcium hydroxide. Although there is known a commercially available root filling paste for dental surgery on the basis of calcium hydroxide which contains an X-ray contrast agent, the degree of filling of the root canals, however, can be determined with difficulty only even in the application of said root filling paste, apparently due to the high ratio of calcium hydroxide to X-ray contrast material. Apart herefrom, the addition of the X-ray contrast material to the root filling paste on the basis of calcium hydroxide does not al all improve the inferior fillability or insertability into the root canals of such paste.

Apparently, the low X-ray contrast and the problems in filling the root filling paste containing calcium hydroxide into the root canals are the principal reason for that the Walkhoff's paste is still given preference to a root filling paste on calcium hydroxide basis (see A. Herforth and M. Strassburg in "Dtsch. zahnärztl. Z.", Vol. 32, pages 453 to 459 (1977)).

It is accordingly the object of the present invention to improve the conventional root filling pastes on the basis of calcium hydroxide to such extent that such pastes may be filled into the root canals of gangrenous teeth without any difficulty, thereby to completely fill the root canals after their application and render possible a determination of the degree of filling of the root canals by X-ray inspection.

Accordingly, subject matter of the invention is a root filling paste for dental surgery comprising calcium hydroxide and an X-ray contrast agent as well as oleum pedum tauri as the paste base.

Advantageously, the root filling paste of the present invention contains barium sulfate as an X-ray contrast material.

A preferred root filling paste according to the invention contains about 55 percent by weight of calcium hydroxide, about 23 percent by weight of barium sulfate as an X-ray agent and about 22 percent by weight of oleum pedum tauri. The proportions of the individual components may vary, depending on the teeth to be filled, generally by ±10%, preferably by ±5% and most preferably by ±2%.

As a rule, in the case of front teeth a higher proportion of calcium hydroxide is used, whereas in the case of molars—in order to obtain sufficient X-ray contrast even in the lateral teeth area—a higher content of barium sulfate on account of the calcium hydroxide is used. In particular, it has to be noted that on the one hand the content of calcium hydroxide should be as high as possible, while on the other hand the lower limit of the barium sulfate content is determined by an X-ray contrast which still provides distinct identification.

The use of oleum pedum tauri in dental surgery is in principle known (cf I. Gruhn, G. Klinger and G. Lange "Prüfung der desinfizierenden Wirkung des Calciumperoxids als Wurzelkanalfüllmaterial", Stomatol, German Democratic Republic, 28 (1978)). This publication reports on the disinfecting action of the calcium peroxide on the root canal and the periapical region.

The cojoint use of calcium peroxide and oleum pedum tauri is contemplated to prevent the instantaneous decomposition of the peroxide and accordingly the possibility for periapical inflammation caused by overpressure. As demonstrated by the relevant test results given below, however, this does not hold true. In the clinical examination or testing of the "medical root filling paste" calcium peroxide/oleum pedum tauri, one week after the filling of the root still 80% of the patients were complaining about periapical pain caused by pressure being due to an exacerbation; this means that the combination of calcium peroxide and oleum pedum tauri, in contrast with the statements according to the above publication, is not suitable as a root filling paste for dental surgery.

Consequently, there was not the least reason for the one skilled in the art to combine the one component of the conventional combination, namely the oleum pedum tauri which in the conventional combination should meet the actually not yet realized function of retarding the oxygen release from the calcium peroxide to such extent that a periapical inflammation caused by over-pressure is prevented from occuring, with two other—admittedly conventional—components of a root filling paste for dental surgery, namely with calcium hydroxide and an X-ray contrast agent. In the light of the abovementioned publication and of the findings gained from the reproduction of the teachings of this publication, it was not obvious for the expert that the combination of calcium hydroxide, X-ray contrast agent and oleum pedum tauri would provide a practically useful root filling paste for dental surgery at all.

Regardless of its high concentration of calcium hydroxide, a root filling paste according to the invention may be filled or applied without difficulty into the prepared root canal and bone defect immediately after the preparation thereof and for some period thereafter, since the paste shows a smooth consistency and is not brittle during such period. Following the application, the root filling paste according to the invention thoroughly fills out the root canals while readily permitting the determination of the degree of filling of the root canals and of the periapical area owing to the high X-ray contrast of the paste.

A root filling paste according to the invention may have incorporated thereinto, if necessary, additives for the treatment of gangrenous teeth, which are customary in the field of dental surgery. Promising is, for instance, an addition of vitamin B in the case of neuritis and neuralgia.

The following Example is intended to explain the invention in greater detail. The invention, however, should not be limited thereto.

EXAMPLE

Using a root filling paste according to the invention, 47 root-canal treatments of front and eye teeth and of premolars were conducted with 33 male and female patients of the age of from 18 to 66 years. Involved were ganrenous teeth affected by chronic-apical parodontitis, which teeth were in a chronical or acutely exacerbative phase. Part of the teeth were already trepaned, while the remainder of the teeth were still in an intact state.

After detailed anamnesis, clinical diagnosis and X-ray inspection with apical setting of each tooth to be treated, a two-phase preparation of the root canal was made, optionally after a customary dental pretreatment. Upon cleaning and disinfection, neutralization and drying of the root canals, the root filling paste according to the invention was introduced into the root canals with the aid of a suitable instrument for dental surgery. At the same time, the root filling paste introduced into the root canals was also advanced through the enlarged foramen apicale into the inflamed periapical tissue.

Following the filling process, the degree of filling was examined by X-ray inspection. It was found that in every instance a correct filling of the root was obtained.

Finally, a composite filling was applied to each tooth.

As the root filling material, a root filling paste (called "Gangraena gap") according to the invention having the following composition was used:

| | | Percent by weight |
|---|---|---|
| (1) Ca(OH)$_2$ | 96% minimum | |
| CaCO$_3$ (calcium carbonate) | 3% maximum | |
| constituents insoluble in hydrochloric acid | 0.1% maximum | 50*–55** |
| Chloride (Cl) | 0.005% maximum | |
| Sulfate (SO$_4$) | 0.2% maximum | |
| Heavy metals (as Pb) | 0.005% maximum | |
| Iron (Fe) | 0.05% maximum | |
| Constituents not precipitable by ammounium oxalate, as sulfate | 2.5% maximum | |
| (2) barium sulfate (pure) | | 28*–23** |
| (3) oleum pedum tauri (pure) | | 22–22 |

*for the filling of molars
**for the filling of front teeth

Five of the gangrenous teeth treated which were affected by apical parodontitis, were at the same time affected, as complication, by fistulae into the vestibule.

In the case of these patients, the treatment involved not only the root filling and the filling of the periapical granuloma, but at the same time also the introduction or filling of the material into the fistula tract. As a positive indication to the success of application, the egress of the material from the fistual tract into the vestibule at transcanalary filling could be observed. This fact likewise demonstrates the ready and safe applicability of the root filling composition according to the invention.

Subsequent examinations and controls showed that among the 33 patients treated of which 29 patients were complaining about pains at the beginning of the treatment, only 12 patients still suffered from mostly trifling pains in the course of the first 24 hours following the treatment. The complaints continued to exist in only two patients during the first week following the treatment, but the pains gradually diminished. Only one female patient who suffered from various severe metabolic diseases, complained of occasionally occuring pains after a period of more than one week.

In addition to the anamnesis of pains, at the time the treatment was started, a more or less marked swelling was observed by inspection and palpation in 11 patients. This swelling fully disappeared in the case of 4 patients within the first day after the treatment, and in the case of 4 other patients in the course of the first week after the treatment. Slight swelling symptoms upon expiration of the first week were found in only 3 patients.

As already indicated, five of the teeth treated shows fistulae into the vestibule at the start of the treatment. One of these fistulae disappeared as a result of the treatment after a period of only 4 weeks, while the other four fistulae disappeared within a period of 2 months.

At the apex, it could be demonstrated by X-ray inspection after 3, 6, 9 or 12 months, that portions which at the beginning of the treatment appeared lighter have returned to their normal condition when inspected by X-rays.

In 9 teeth, clinically a hard tissue barrier was found, and an apical occlusion was observed by X-ray inspection. These teeth were finally root-filled.

One tooth was post-fixed 6 months after the root treatment. In this instance, the root treatment merely formed the preparation for the post fixation which was contemplated at the very start of the treatment.

COMPARATIVE EXAMPLE

Test results of a comparative in-vivo treatment with calcium peroxide/oleum pedum tauri or with the root filling paste according to the invention, respectively:

10 patients were each given a root filling by using calcium peroxide/oleum pedum tauri and the root filling paste according to the invention, respectively. After one week, 80% of the patients treated with calcium peroxide/oleum pedum tauri still suffered from periapical pain caused by pressure resulting from an exacerbation. In contrast, among the patients treated with the root filling paste according to the invention, 60% of them were free from pains already after one day, and at least 90% of them were free from pains after one week.

The embodiments of the invention described herein are intended as illustrative of applicants' novel concept and hence all those variations and modifications which are obvious to one of ordinary skill in the art are considered to be within the scope of the invention.

What we claim is:

1. A root filling paste for dental surgery comprising from about 45 to 65% by weight calcium hydroxide, from about 13 to 33% by weight of an X-ray contrast agent, and from about 12 to 32% by weight oleum pedum tauri.

2. The root filling paste of claim 1 wherein said X-ray contrast agent is barium sulfate.

3. The root filling paste of claim 1 further including an effective amount of vitamin B.

4. The root filing paste of claim 2 wherein said calcium hydroxide is present at from 50 to 60% by weight; said barium sulfate is present at from 18 to 28% by weight, and said oleum pedum tauri is present at from 17 to 27% by weight.

5. The root filling paste of claim 1 wherein said calcium hydroxide is present at from 53 to 57% by weight; said barium sulfate is present at from 21 to 25% by weight, and said oleum pedum tauri is present at from 20 to 24% by weight.

* * * * *